United States Patent [19]
Betts et al.

[11] Patent Number: 5,569,367
[45] Date of Patent: Oct. 29, 1996

[54] APPARATUS FOR SEPARATING A MIXTURE

[75] Inventors: Walter B. Betts, Newton-Upon-Derwent; Jeremy J. Hawkes, Fishergate, both of England

[73] Assignee: British Technology Group Limited, London, England

[21] Appl. No.: 318,786
[22] PCT Filed: Apr. 15, 1993
[86] PCT No.: PCT/GB93/00793
  § 371 Date: Jan. 27, 1995
  § 102(e) Date: Jan. 27, 1995
[87] PCT Pub. No.: WO93/20927
  PCT Pub. Date: Oct. 28, 1993

[30] Foreign Application Priority Data

Apr. 16, 1992 [GB] United Kingdom ............... 9208357

[51] Int. Cl.$^6$ .................................................. G01N 27/26
[52] U.S. Cl. .................... 204/547; 204/643; 204/600; 204/450
[58] Field of Search ............... 204/299 R, 180.1, 204/183.1, 180.5, 547, 643

[56] References Cited

U.S. PATENT DOCUMENTS

| | | | |
|---|---|---|---|
| 3,795,605 | 3/1974 | Candor | 204/183.1 |
| 3,893,898 | 7/1975 | Candor | 204/183.1 |
| 4,061,560 | 12/1977 | Hannig et al. | |
| 4,326,934 | 4/1982 | Pohl | 204/183.1 |
| 4,441,972 | 4/1984 | Pohl | |

FOREIGN PATENT DOCUMENTS

| | | |
|---|---|---|
| 2508844 | 9/1976 | Germany . |
| 9002792 | 3/1990 | WIPO . |
| 9108284 | 6/1991 | WIPO . |

*Primary Examiner*—Kathryn Gorgos
*Assistant Examiner*—Alex Noguerola
*Attorney, Agent, or Firm*—Cushman, Darby & Cushman

[57] ABSTRACT

Apparatus for separating a mixture of particles comprising a chamber with an inlet and an outlet, means for providing an eluant flow between said inlet and said outlet, within the chamber an electrode structure of at least two electrodes, means for applying an alternating voltage between the electrodes, said electrode structure being such that when energized in operation of the apparatus there is established in the eluant a spatially non-uniform alternating field, whereby particles caused to flow through the chamber in said eluant flow are carried past the electrode structure and are separated into fractions. There may be an ancillary electrode structure of at least two electrodes placed upstream of the main electrode structure with regard to the direction of the flow of fluid. At least one of the electrodes of the electrode structure may be comprised of one or more grid like structures. The electrode structure may be comprised of interleaved grid like structures aligned to obstruct straight through flow.

11 Claims, 5 Drawing Sheets

APPARATUS FOR SEPARATING A MIXTURE

This invention relates to a method and apparatus for the separation of particles, including micro-organisms, utilising the phenomenon of dielectrophoresis.

It is well known that dielectrically polarisable particles in a non-uniform electrical field are subject, even If they have no net charge, to a "dielectrophoretic" force if the effective polarizability of the particles is different to that of the surrounding medium. The movement is determined by the dielectric properties (conductivity and permittivity) rather than by the charge of the particles, as in the wider known phenomenon of electrophoresis. The force F to which a particle of volume v and effective polarizability p is subject is given by the relation $$F=pv(E.\nabla)E$$

where E is the electric field strength at the position of the particle and $\nabla$ is the del vector operator.

In an alternating field in which the field strength at any point is oscillatory but the field pattern remains stationary, the dielectrophoretic force on a particle is oscillatory but unidirectional, even though the electric field varies cyclically. The particles, if they are polarisable more than the medium in which they are suspended move In the direction of increasing electric field strength which means, usually towards one of a plurality of electrodes between which the field is established. The polarizability of a particle, and therefore the polarity and magnitude of the dielectrophoretic force upon it, will vary as a function of the frequency of the applied field because the dielectric properties of all materials have characteristic frequency dependent components.

Separators such as column separators employ a matrix to retain the particles temporarily as they flow through the column; the retention time is dependent upon a physical property of the particle. As a mixture of particles passes through the matrix different types of particles are retarded at different rates and separate into fractions. In chromatographic separators the retardation of the particles is caused by their size and in ion exchange separators the retardation of particles is dependent upon their ionic strength. Electrophoretic separators rely on the charge carried by the particles and neutral particles must first be given a charge before the separation can occur. The charged particles are then passed through a matrix under the influence of an electric field, which retards the different types of particles according to their size and charge. In all of these separators the order in which the fractions are passed out is constrained and depends upon the type of separator and the type of matrix.

The known devices for dielectrophoretic spectra analysis are designed to retain the particles between the electrodes for the examination of some property of the collected particles in order to determine the type or quantity of particles present. However, a long retention time increases the probability of the particles (especially cells) sticking permanently to the electrodes.

Separation of charged particles by electrophoresis as described by U.S. Pat. No. 4,061,560, requires the use of a buffer solution and the zeta potential of the system is influenced by the introduction of electrolytes to the buffer solution.

U.S. Pat. No. 4,441,972 discloses techniques for the breakdown of cells and subsequent fusing of the contents of contiguous cells. It also teaches separating or sorting of cells for examination only, the cells being thereafter collected and withdrawn.

According to one aspect of the invention there is provided apparatus for separating a mixture of particles comprising a chamber with an inlet and an outlet, means for providing an eluant flow between said inlet and said outlet, within the chamber an electrode structure of at least two electrodes, means for applying an alternating voltage between the electrodes, said electrode structure being such that when energized in operation of the apparatus there Is established in the eluant a spatially non-uniform alternating field, whereby particles caused to flow through the chamber In said eluant flow are carried past the electrode structure and are separated into fractions.

As the particles are carried through the chamber, different types of particles are retarded differentially and are separated into discrete bands of particles.

The apparatus may also include means for inducing a sample into the chamber. The means to provide the eluant flow through the chamber may be a pump or gravity.

According to another aspect of the invention there is provided a method for separating a mixture of particles comprising providing In a chamber a spatially non-uniform alternating electric field, providing a flow of eluant through the chamber and the field, eluting a limited sample of said mixture with said eluant, passing the eluted sample through the electric field, causing or permitting the different types of particles in the mixture to be retarded differentially and producing a flow of fractions of different types of particles separated by a flow of eluant.

The method may include applying to the electrode structure an alternating voltage at a single frequency, usually selected as the optimum by some previous investigation. When the electric field is alternating at a particular frequency the different types of particle experience different dielectrophoretic forces due to the differences in their polarizability. Thus the flow of each type of particle through the chamber will be retarded differently due to the variations in attractive forces experienced by each type of particle as it passes over the electrode structure. As a result the mixture separates into bands or fractions of different types of particles as the eluant washes each type of particle through the chamber at a different rate.

The dielectrophoretic force, and thus the retardation, experienced by a particle flowing through the chamber is dependent upon the pH and the conductivity of the eluant and the frequency of the voltage applied to the electrode structure. Altering the frequency of that voltage may alter the order in which the particles are separated and the degree of separation.

A further degree of flexibility may be achieved by switching the signal to the electrode structure on and off. This pulsing of the signal may sharpen the elution bands without extending the time taken for the particles to pass through the chamber, and lessen the probability of a charge transfer causing the particles to stick permanently to the electrode structure. It may also prevent the formation of clusters of particles which behave differently from single particles and thus interfere with the expected operation of the apparatus. Upon completion absolute removal of particles can be ensured by switching the electrodes off and passing further volumes of eluant or other fluid past at a high rate.

According to another aspect of the invention there is provided a method of forming a uniform starting band at the head of the electrode structure of the apparatus described above comprising passing a flow of particles in suspension through the electrode structure, energizing said electrode structure for a defined length of time with a voltage high enough to collect a variety of particles in an initial part of the electrode structure as a band and then reducing the voltage, causing or permitting the band of collected particles to be washed along the chamber for separation action.

According to another aspect of the invention there is provided a method of forming a uniform starting band at the head of the electrode structure of the apparatus described above comprising placing upstream of the main electrode structure with regard to the direction of the flow of fluid an ancillary electrode structure of at least two electrodes, energizing said ancillary structure for a defined length of time with a voltage high enough to collect a variety of particles on said ancillary electrode structure, reducing the voltage to the ancillary electrode structure and applying an energizing voltage to the main electrode structure, causing or permitting the band of collected particles to be washed along the column housing for separation action.

According to a further aspect of the invention there is provided apparatus for collecting from a mixture of particles in suspension an increased concentration of a particular type of particle comprising a chamber with a inlet and an outlet, means for providing a flow of the mixture between said inlet and said outlet, an electrode structure of at least two electrodes within the chamber, means for applying an alternating voltage between the electrodes, said electrode structure being energizable to establish in the fluid a spatially non-uniform alternating field, first at a field strength high enough to collect a uniform starting band of particles in an initial part of the electrode structure and thereafter at a reduced level, whereby particles caused to flow through the chamber are carried past the electrode structure and are separated into discrete bands with a greater concentration of a particular type of particle.

According to yet another aspect of the invention there is provided a method for collecting from a mixture of particles in suspension an increased concentration of a particular type of particle comprising providing in a chamber a spatially non-uniform alternating electric field, providing a flow of the mixture in suspension through the chamber and the field, passing the mixture in suspension through the electric field, the electric field being high enough to collect a uniform starting band of particles in an initial part of the chamber and then reducing the strength of the electric field so that the collected starting band of particles may be washed through the chamber, thereby causing or permitting the different types of particle to be retarded differentially and producing a flow of the mixture containing discrete bands with a greater concentration of a particular type of particle separated by a flow of the fluid.

In the apparatus and method last recited the mixture of the different types of particles in suspension is used as the eluant and although each band of particles that elutes from the chamber will contain a greater concentration of one particular type of particle than in the original mixture, all of the other types of particles will be present in the band to some extent.

According to another aspect of the invention there is provided a method of selecting from a mixture containing different types of particles in suspension, and other materials particles with a specific range of characteristics, comprising passing the mixture through the electrode structure of the apparatus described above, energizing said electrode structure for a defined length of time with a voltage high enough to collect particles of different types on the electrode structure and then reducing the voltage, thus causing or permitting the collected particles to be washed out of the column housing for separation or identification at a later time.

Instead of collecting the uniform starting band of particles on the main electrode structure, an ancillary electrode structure may be used, as described above. If an ancillary electrode structure is provided, once the voltage to the ancillary electrode structure has been reduced and the collected particles are washed off the ancillary electrode structure, the ancillary electrode structure may be re-energised at a voltage high enough to collect particles. If the voltage and frequency applied to the ancillary electrode structure have been selected to collect all particles in the eluant, the eluant flowing through the chamber will be free of all particles in the original mixture. In this manner each band of particles which elutes from the chamber will be suspended in pure eluant.

According to another aspect of the invention there is provided an electrode housing comprising a transparent substrate, a layer of electrode material placed on said substrate, the electrode material having the form of an electrode structure of at least two electrodes, a transparent cover over the electrode material and separating means placed between the substrate and the cover, said separating means and cover creating with the substrate a sealed channel over the electrode structure with an inlet and an outlet, the housing having, near said outlet, a path through the channel for a beam of electromagnetic radiation to pass without obstruction from the electrode structure.

Alternatively, at least one of the electrodes may be comprised of a one or more grid like structures which are arranged in the chamber so that the particles in the eluant flow are carried substantially through the grid like structures.

The frequencies referred to above are typically in the range 10 Hz to 10 Mhz or more, and when pulsed the pulses may be of the order of 30 seconds.

Two or more electrode housings may be used together.

Embodiments of the invention will now be described by reference to the accompanying drawings, in which.

Figure 1:
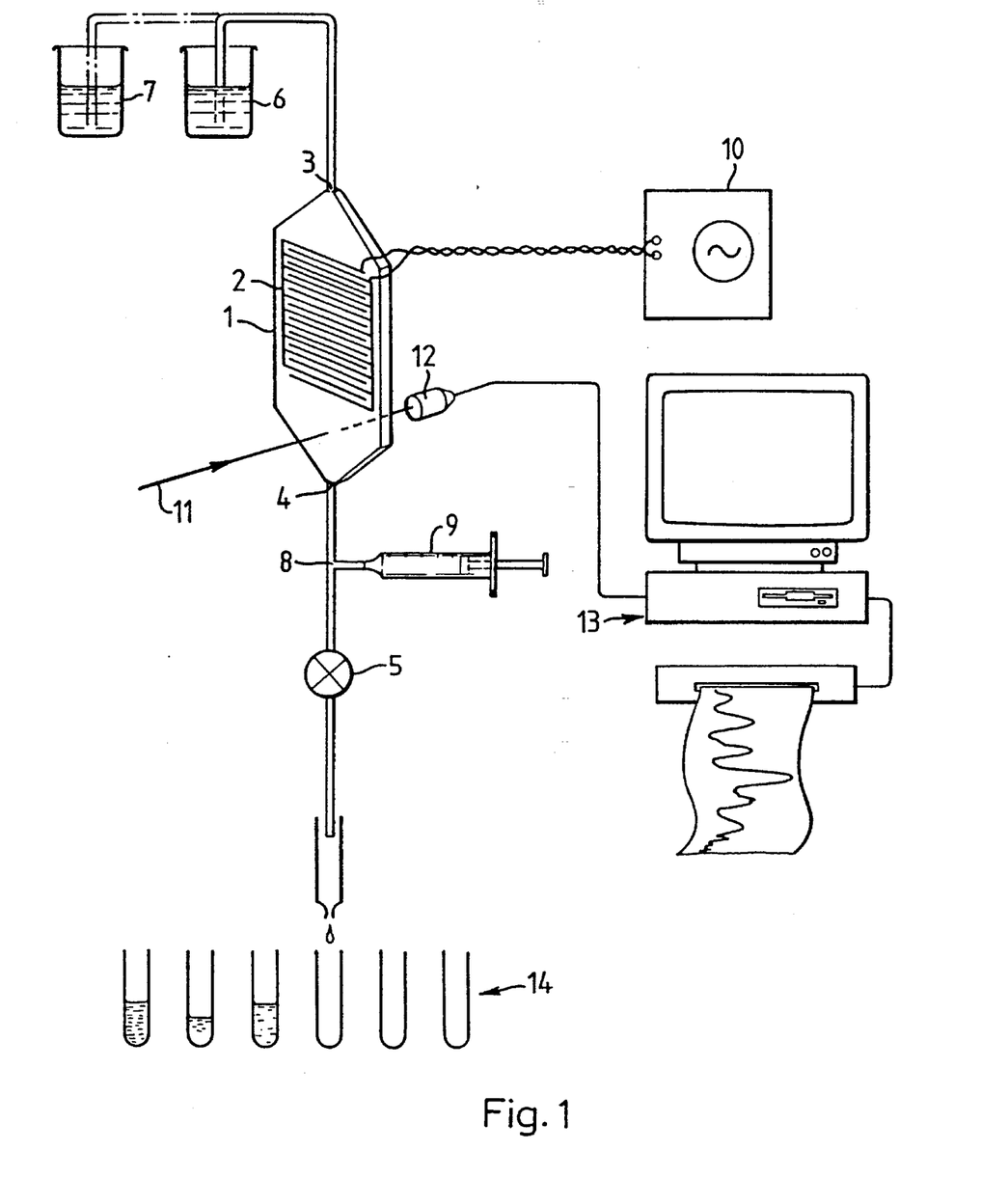
FIG. 1 shows in outline apparatus which can be used either for separating a sample or the initial formation of a sample.

As shown in FIG. 1 an electrode housing (1) of any suitable form is provided with an electrode structure (2) and a fluid flow path is arranged through the electrode housing from an input (3) to an output (4). The electrode structure is described in detail below. A pump (5), conveniently of the peristaltic type, may be used at the output of the electrode housing to draw the fluid through the electrode housing and past the electrode structure. The fluid maybe a mixture of independent types of particles in suspension in a fluid or an eluant and respective sources of these fluids (6) and (7) are arranged for selective connection to the input of the column housing. If the apparatus is to be used for separating the independent types of particles into pure fractions, like a conventional column separator, then the electrode housing is connected first to the sample and thereafter to the eluant. In this mode of operation the output of the electrode housing may be provided with a connection (8) for a syringe (9) or like device for drawing a sample of a defined size into the column. If the apparatus is to be used for collecting one particular particle type from the sample, or selecting particles with a specific range of characteristics, such as size, shape, density, etc., then the electrode housing is connected exclusively to the mixture. The apparatus also Includes a signal generator (10) or other source or alternating voltage to produce an alternating voltage, usually of a few tens of volts, which is applied to the electrode structure (2). Conveniently, this voltage produces a electric field of at least 200 Kv/m across the electrode structure and has a frequency which ranges from 10 Hz to 10 MHz or more. It may not be necessary to provide this full range in all embodiments.

The electrode structure may be overlaid with strips of a thick photoresist to form channels along the direction of flow, which guide the bands of cells passing down the column housing and prevent flow dynamics from breaking up a band of cells as it passes through the column housing. Alternatively, the electrode structure may be overlaid with a smooth, non-stick coating to prevent horizontal misalignment of a band of cells as it passes through the column housing.

Also provided is a light source (not shown) which is arranged to project a beam of light (11) or other radiation through the electrode housing, at a location downstream of the electrode structure, and a light detector (12) or like device sensitive to the intensity of the light beam after transmission through the chamber. The light detector is thus sensitive to the increase or decrease in absorption or scattering of the light beam which indicates an increase or decrease in the concentration of the particles suspended in the fluid traversed by the light beam at the said location. The light detector is conveniently attached to a recording device (13) such as a computer or chart recorder, the output of which represents the measured intensity of the light beam against time. Thus the presence of bands of separated particles is indicated as they pass out of the electrode housing and may be collected in a fraction collector (14). Alternatively, the light detector may be a light microscope with associated image analysis. The total time taken for each run of the separator is typically less than 10 seconds. Several electrode housings may be used in series to obtain a finer degree of separation or in parallel to increase the volume to be separated.

It may be desirable to form a uniform starting band of the sample at the head of the electrode structure. The electrode structure is energized for a defined length of time with a voltage high enough to collect particles on the first few electrodes, say 10–20 volts. The voltage is then reduced, to say 5 volts, causing the uniform starting band to be washed along the structure allowing separation to occur.

Figure 2:
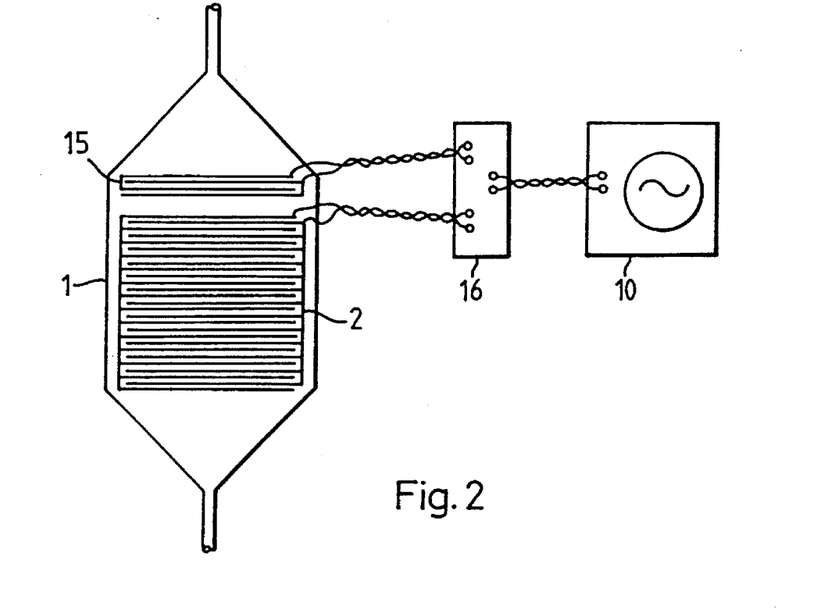
FIG. 2 shows in outline an alternative electrode housing usable in the apparatus of FIG. 1 which can be used for separating a sample.

An alternative to the electrode housing described in FIG. 1 is shown in FIG. 2. An ancillary electrode structure (15) is placed in the column housing (1), upstream of the main electrode structure (2) with regard to the direction of the flow of fluid. The ancillary electrode structure may be energized by the signal generator (10) through a switch (16) for a defined length of time with a voltage high enough to collect particles on said ancillary electrode structure, say 10–20 volts. The voltage on the ancillary electrode structure is then reduced and the voltage to the main electrode structure switched on, causing the uniform starting band to be washed along the column housing and allowing separation to occur. If the voltage on the ancillary electrode structure is then returned to a voltage high enough to collect all particles in the fluid as soon as the starting band has been washed off the ancillary electrode structure, all particles flowing past the ancillary electrode structure will be collected. The fluid washing the starting band along the rest of the electrode housing will be free of all particles (and thus be pure eluant) and the output of the column housing will be fractions in pure eluant.

The electrode housing may also be used as a pre-filter for an identification system or another separation system, which may even be another column housing. The electrode structure is energized for a defined length of time with a voltage, say 10–20 volts, high enough to collect a sample of different types particles with a specific range of characteristics on the electrode structure. The voltage is then reduced, allowing the sample to be washed out of the electrode housing.

The output of the electrode housing, whether it is a pure fraction in eluant, an increased concentration of one particular particle type in the mixture or a selection of particles with a specific range of characteristics, may be diverted into a dielectrophoretic apparatus loop, substantially as described in British patent application number 8926781, for frequency scanning and production of a pure spectrum. It may also be possible to identify the type of particle from a previously determined characteristic retention time.

Figure 3:
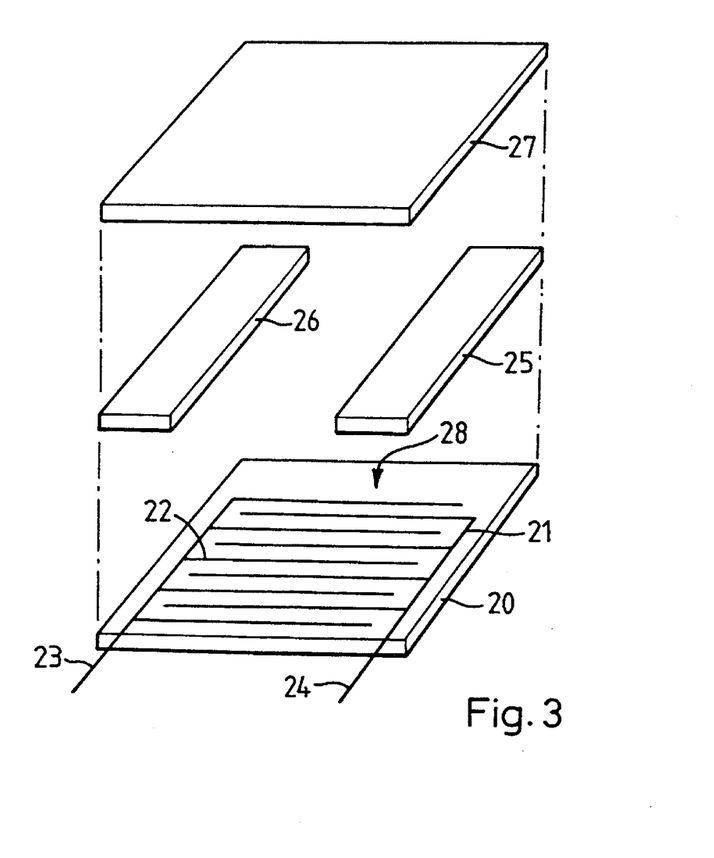
FIG. 3 shows an exploded view of an electrode housing, usable in the apparatus of FIG. 1 or FIG. 2.

As shown in FIG. 3, the electrode housing may be formed by etching a layer of suitable electrode material, such as aluminum, which has been deposited, typically to a thickness of 1 mm, on a transparent substrate (20), such as a microscope slide. The etched layer forms two electrodes with interdigitated fingers (21) and (22) and connection tabs (23) and (24), such that the distance between any two adjacent fingers of an electrode Is approximately 50 μm. By placing two elongate spacer blocks (25) and (26) with a thickness of about 100 μm and separated by between 2–5 mm on the electrode structure, so that the ends of the fingers of one electrode and the junctions of the fingers of the other electrode are covered by the same block, a path for a fluid flow 1s created. The spacer blocks are overlaid with a transparent cover (27) to provide a sealed channel, with an inlet and an outlet, for the flow of fluid over the electrode structure. The dimensions of the channel (2–5 mm wide, 100 μm high and 5 cm long) may vary within a wide range depending upon the sizes of suspended particles which may be encountered. The central part of the length of each finger Is In contact with the fluid disposed therein, though a protective film of non-stick material may be provided to prevent actual contact between the fluid and the electrodes. Strips of photoresist forming channels to guide the flow of particles suspended in the fluid along the electrode structure may be provided, thus preventing misalignment of the bands of particles formed, caused by imperfections In the fluid path. A region (28) of the channel near the outlet is provided through which a beam of light such as ultraviolet light may be arranged to shine without obstruction from the electrode structure.

Figure 4:
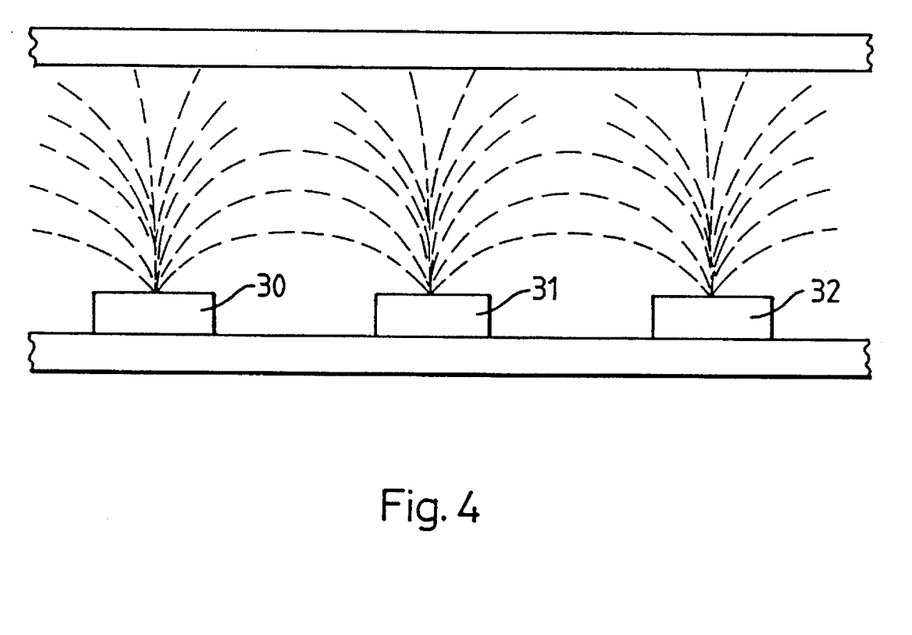
FIG. 4 shows the spatially non-uniform electric field created by the electrodes.

The shape of the electrodes is such as to provide a spatially very non-uniform electric field in their immediate vicinity when a voltage is applied between them, as shown in a generalised form in FIG. 4. In operation, the voltage applied between the pair of electrodes (30 and 31) must produce a spatially non-uniform electric field in the whole channel so that all the particles flowing through the channel are affected. For an electrode housing of the sort described above a signal generator such as a Hewlett Packard 8116A, running at an indicated output of some 16 volts will produce a noticeable separation for a mixture of for example, live and dead yeast.

As mentioned above, the electrode structure may be of aluminium, and formed by depositing a layer of the metal on the substrate and then etching to provide the required electrode pattern. Instead of aluminum, platinum or gold-plated chromium electrodes may be employed, produced either by an etching technique or by a "lift-off" technique in which a pattern mask is formed on the substrate, using a suitable material such as a photoresist material, before a metal layer is deposited and unwanted regions of deposited metal are then removed by removing the pattern mask so as to leave the metal only where it was deposited directly on the substrate.

The electrode structure described above is for use in separating cells in the order of a few microns in diameter, e.g. yeast cells which are typically 10 μm. Finer electrode spacings, such as 5 μm, are possible and may be suitable for bacteria which typically have a diameter of 0.5 μm, but care is required in the manufacture of finer electrode structures to avoid short circuits and broken electrode fingers.

Figure 5:
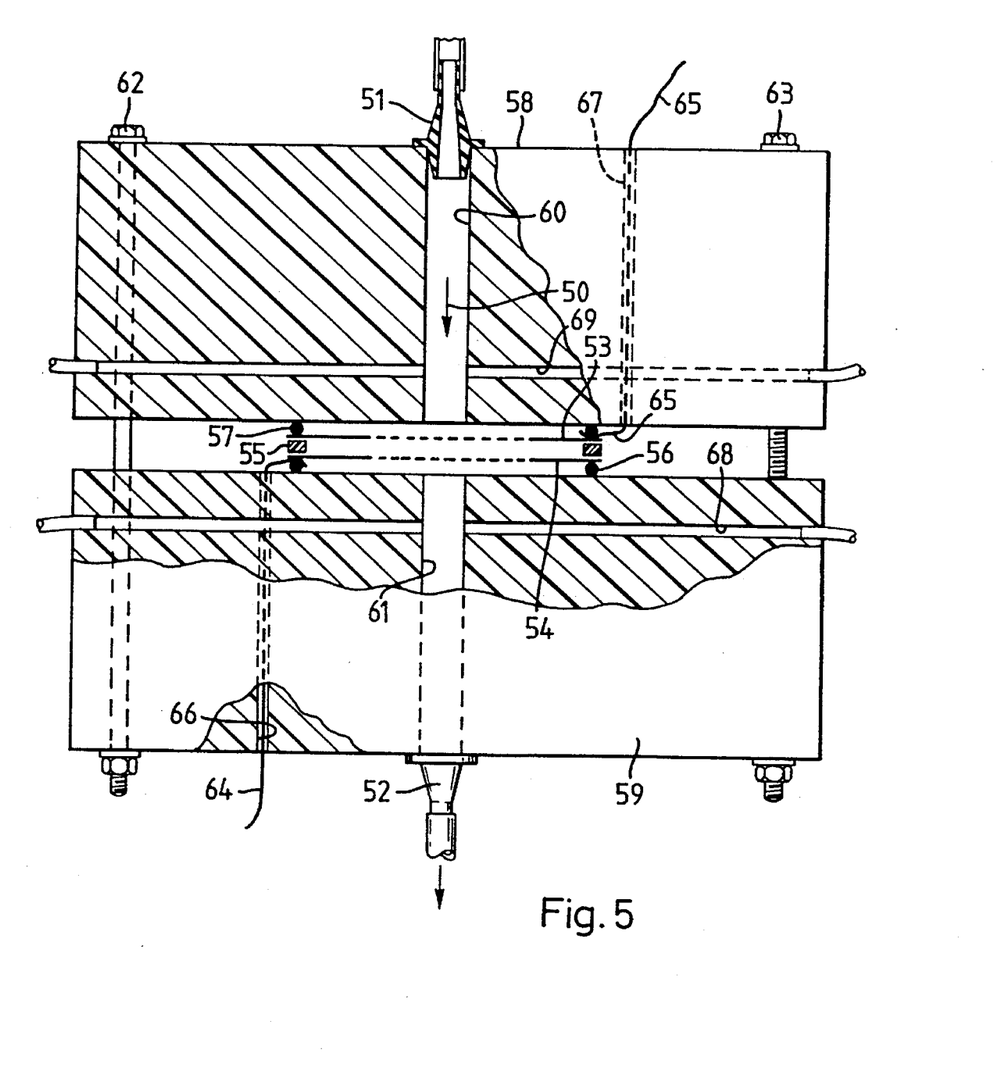
FIG. 5 shows an alternative ancillary electrode structure in a chamber.

FIG. 5 shows (not to scale) a chamber containing an alternative ancillary electrode structure. A fluid path (50) is provided from an input (51) to an output (52), through two grid-like electrodes (53)(54). The two grid electrodes are spaced apart from each other by a spacer (55)(which may be for example a PTFE ring) and are held against this spacer by two O-rings, (56) and (57). The O-rings are in turn held between the two halves of the chamber (58) and (59), through which two bores (60) and (61) provide the input and the output. The two halves are forced together by two bolts (62) and (63) which provide the force to hold the O-rings, the grids and the spacer in place. A copper contact (64, 65) touches one side of each grid electrode and is trapped between the grid and the O-ring. Each contact passes through a bore (66, 67) in each half and is connected to the signal generator (as shown previously in FIG. 1). Further leakage is prevented by sealing the joint between the two halves of the chamber with a sealant, such as a silastic sealant, which is easily broken for disassembly and electrode replacement.

In this example the grid is 150 μm thick, the spacer width is between 200–250 μm (although it may be as little as 8 μm) and the total grid-spacer-grid width is 0.56 mm±0.02 mm. Suitable grids are stainless steel sheets which have been photolithographically etched to produce a gauze like structure of circular holes. The grids, which are 13 mm in diameter, have 20 holes per $mm^2$ and each hole has a diameter of approximately 150 μm. The grids may be plated with a suitably conductive material, such as gold or aluminium. An alternating voltage of 16 V pk-to-pk is applied to the grids by a signal generator, not shown and a frequency in the range of 1 kHz to 1 MHz may be used.

Detection of the particles may be achieved by spectrophotometric means as described in British Patent application number 8926781 and a bore for a fibre optic link to spectrophotometric means is provided in each half of the chamber. The fibre optic cables may be connected to a microscopical detector, not shown.

The electrode housing shown in FIG. 5 may be used as the ancillary electrode structure described above. A band of collected particles may be released to flow past the main electrode structure, and by switching the voltage to the grids back up to a voltage high enough to collect all particles in the fluid, the eluant flowing out of the grids and thus past the main electrode structure, will be particle free of particles. If the electrode housing Is used in such a way, it is possible to collect particles in sufficient numbers that further analysis is possible. Current methods involve laborious filtration and centrifugation.

Figure 6:
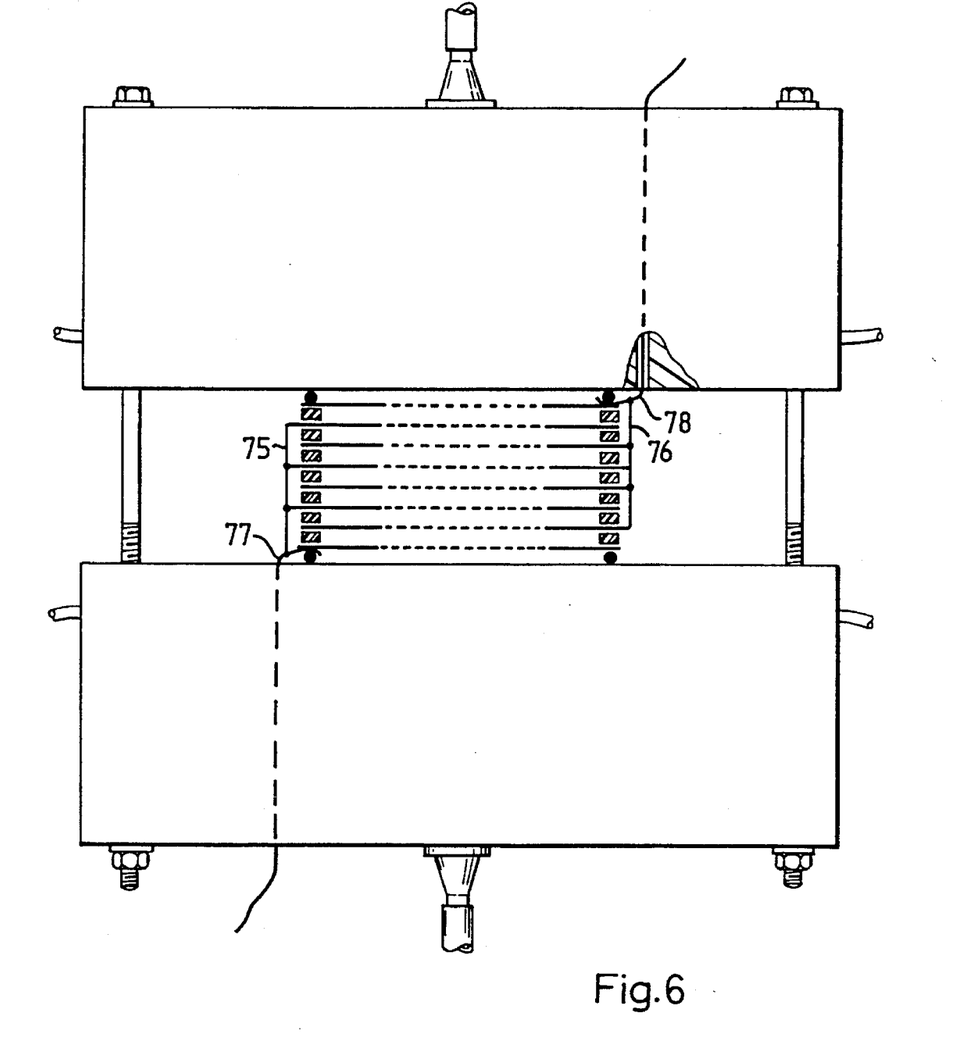
FIG. 6 shows another main electrode structure in a chamber.

The main electrode housing may alternatively be provided with an array of spaced apart grids (75, 76) as shown in FIG. 6 connected to the signal generator by copper contracts (77, 78) such as to provide a three dimensional electrode structure of interleaved grids electrodes.

In both the two grid and multiple grid arrangements it is preferable that the apertures are not aligned, avoiding a "straight through" flow path.

While the invention has described with respect to a specific embodiment it will be appreciated that variations, such as in the shape of the electrode housing or in the construction of electrode structure, may be made without departing from the ambit of the invention.

We claim:

1. Apparatus for separating a mixture of particles by selective retardation of some of the particles comprising:

a chamber with an inlet and an outlet, means for providing an eluant flow between said inlet and said outlet, an electrode structure of at least two electrodes disposed within the chamber, means for applying an alternating voltage between the electrodes, said electrode structure being such that when energized in operation of the apparatus there is established in the eluant a spatially non-uniform alternating field, where particles caused to flow through the chamber in said eluant flow are carried past the electrode structure and are separated into fractions, wherein an auxiliary electrode structure is placed upstream of the main electrode structure, the auxiliary electrode structure being energized in use, such that substantially all the particles are collected into a relatively small volume.

2. Apparatus as claimed in claim 1, wherein said means for providing the eluant flow through the chamber includes a pump.

3. Apparatus as claimed in claim 1, wherein said means for providing the eluant flow through the chamber uses the force of gravity.

4. Apparatus as claimed in claim 1 in which at least one of the electrodes of the electrode structure is comprised of one or more structures in the form of a grade.

5. Apparatus as claimed in claim 1, wherein the electrode structure comprises interleaved, structures in the form of a grid, aligned to obstruct straight through flow.

6. Method for separating a mixture of particles using an apparatus including a chamber; a main electrode structure of at least two electrodes disposed within the chamber; means for applying an alternating voltage between the electrodes, and an ancillary electrode structure disposed upstream of the main electrode structure, the method including:

providing a spatially non-uniform alternating electric field in the chamber, providing a flow of eluant through the chamber and the electric field, eluting a limited sample of said mixture with said eluant, passing the eluted sample through the electric field, causing or permitting the different types of particles in the mixture to be retarded differentially; and producing a flow of fractions of different types of particles separated by the flow of eluant, wherein a uniform starting band of mixture is formed upstream of the said spatially non-uniform field by energizing the ancillary electrode structure for a length of time with a voltage sufficiently high enough to collect particles in a starting band, and then reducing the voltage, thus causing or permitting the starting band to be washed along the chamber for separation.

7. Method as claimed in claim 6 including altering the frequency of the non-uniform alternating electric field to alter the order in which the particles are separated.

8. Method as claimed in claim 7, including altering the frequency of the non-uniform alternating electric field to alter the degree of separation between each of the fractions with a greater concentration of one particular type of particle to some extent.

9. Method as claimed in claim 6 including switching the non-uniform alternating electric field on and off to sharpen the fractions with a greater concentration of one particular type of particle.

10. A method for forming a uniform starting band in a process of separating a mixture of particles using an apparatus including a chamber; an electrode structure of at least two electrodes disposed within the chamber; and means for applying an alternating voltage between the electrodes, the method including:

forming the uniform starting band at the head of the electrode structure by passing a flow of particles in suspension through the electrode structure, energizing the electrode structure for a defined length of time with a voltage high enough to collect particles in an initial part of the electrode structure as a band and then reducing the voltage, causing or permitting the band of collected particles to be washed along the chamber for separation action.

11. Method as claimed in claim 10, wherein the electrode structure includes an ancillary electrode structure which is re-energized once the band of previously collected particles has been washed-off the ancillary electrode structure.

* * * * *